United States Patent
Lance et al.

(10) Patent No.: US 12,042,438 B2
(45) Date of Patent: Jul. 23, 2024

(54) VACUUM PAD AND RELATED SYSTEM

(71) Applicant: ORLANDO HEALTH, INC., Orlando, FL (US)

(72) Inventors: Teresa Lance, Orlando, FL (US); Neeraj Desai, Windmere, FL (US); Neil Whitehouse, North Kingstown, RI (US)

(73) Assignee: Orlando Health, Inc., Orlando, FL (US)

( * ) Notice: Subject to any disclaimer, the term of this patent is extended or adjusted under 35 U.S.C. 154(b) by 0 days.

(21) Appl. No.: 17/819,846

(22) Filed: Aug. 15, 2022

(65) Prior Publication Data
US 2023/0114026 A1    Apr. 13, 2023

Related U.S. Application Data

(63) Continuation of application No. 17/499,346, filed on Oct. 12, 2021, now Pat. No. 11,413,206.

(51) Int. Cl.
*A61G 13/00*    (2006.01)
*A61G 13/10*    (2006.01)
*A61M 1/00*    (2006.01)

(52) U.S. Cl.
CPC ....... *A61G 13/102* (2013.01); *A61G 13/0009* (2013.01); *A61M 1/73* (2021.05); *A61G 2203/30* (2013.01)

(58) Field of Classification Search
CPC ...... A61G 13/00; A61G 13/10; A61G 13/102; A61G 13/0009; A61G 2203/30; A61M 1/73

See application file for complete search history.

(56) References Cited

U.S. PATENT DOCUMENTS 3,757,356 A * 9/1973 Freeman ................. A61G 7/02
                                                                      4/456
3,889,302 A * 6/1975 Ketterer ................. A61F 13/00
                                                                      5/604

(Continued)

FOREIGN PATENT DOCUMENTS

CN    101972511 A    2/2011
CN    208905848 U    5/2019

(Continued)

OTHER PUBLICATIONS

Extended European Search Report for EP Application No. 21211975.4 dated May 27, 2022 (8 pages).

*Primary Examiner* — Fredrick C Conley
(74) *Attorney, Agent, or Firm* — Crowell & Moring LLP

(57) ABSTRACT

A vacuum pad may include a top layer forming a top surface of the vacuum pad; a bottom layer forming a bottom surface of the vacuum pad; and a plurality of spacers located between the top layer and the bottom layer such that an interior space is formed between the top layer and the bottom layer. The interior space may have at least one channel extending around at least one spacer of the plurality of spacers. The vacuum pad may also include an outlet tube in fluid communication with the interior space, where the top layer includes a plurality of holes. A vacuum system may include the vacuum pad along with a canister and a vacuum source for moving fluid from the vacuum pad to the canister.

20 Claims, 12 Drawing Sheets

(56) References Cited

U.S. PATENT DOCUMENTS

| | | | | |
|---|---|---|---|---|
| 4,870,710 A | * | 10/1989 | Hartmann | A61F 5/48 5/501 |
| 5,176,667 A | * | 1/1993 | DeBring | A61B 46/00 4/144.1 |
| 5,437,651 A | * | 8/1995 | Todd | A61M 1/915 604/323 |
| 5,655,258 A | * | 8/1997 | Heintz | A61G 13/102 604/317 |
| 5,827,246 A | * | 10/1998 | Bowen | G03B 27/60 604/313 |
| 5,870,797 A | | 2/1999 | Anderson | |
| 6,102,073 A | | 8/2000 | Williams | |
| 7,043,792 B2 | | 5/2006 | Kessler | |
| 7,192,409 B2 | | 3/2007 | Lorenzo | |
| 7,416,576 B2 | | 8/2008 | Ziebold et al. | |
| 7,723,559 B2 | | 5/2010 | Linnane et al. | |
| 7,905,870 B2 | | 3/2011 | Harty | |
| 8,215,929 B2 | | 7/2012 | Shen et al. | |
| 9,408,755 B2 | | 8/2016 | Larsson | |
| 11,000,418 B2 | | 5/2021 | Dunn | |
| 2002/0065494 A1 | * | 5/2002 | Lockwood | A61M 1/92 604/327 |
| 2005/0148913 A1 | * | 7/2005 | Weston | A61M 1/964 602/2 |
| 2011/0123758 A1 | | 5/2011 | Pollaud et al. | |
| 2017/0028113 A1 | * | 2/2017 | Shuler | A61F 13/00068 |
| 2019/0151159 A1 | | 5/2019 | Gowans et al. | |

FOREIGN PATENT DOCUMENTS

| | | |
|---|---|---|
| EP | 0 300 621 A1 | 6/1988 |
| WO | WO 2014/014842 A1 | 1/2014 |

* cited by examiner

025
VACUUM PAD AND RELATED SYSTEM

RELATED APPLICATION(S)

This application is a continuation of U.S. patent application Ser. No. 17/499,346, filed Oct. 12, 2021, entitled "VACUUM PAD AND RELATED SYSTEM," and set to issue on Aug. 16, 2022 as U.S. Pat. No. 11,413,206. The application listed in this paragraph is hereby incorporated by reference in its entirety.

TECHNICAL FIELD

The present disclosure relates to a device for collecting and monitoring fluid loss in a medical procedure, such as a mother's blood loss during a caesarean delivery. In particular, the present disclosure relates to a vacuum pad and related system.

BACKGROUND

A human or animal patient may experience fluid loss in a variety of situations, particularly in surgical procedures. For instance, some women experience moderate to severe bleeding from the uterus during a Cesarean delivery ("C-section"). While a certain amount of bleeding is normal and safe, (e.g., an average C-section is associated with about four cups of blood loss), excess blood loss can be dangerous. Other fluid losses that may need to be addressed included losses of amniotic fluid, vaginal discharge, etc. To complicate matters, the patient is often covered by a surgical drape, which may limit the surgeon's ability to monitor fluid loss visually. To address these issues, the present disclosure relates to a device for collecting and monitoring fluid loss in a medical procedure.

BRIEF DESCRIPTION OF THE DRAWINGS

The embodiments discussed herein may be better understood with reference to the following drawings and description. The components in the figures are not necessarily to scale. Moreover, in the figures, like-referenced numerals designate corresponding parts throughout the different views.

DETAILED DESCRIPTION

Figure 1:
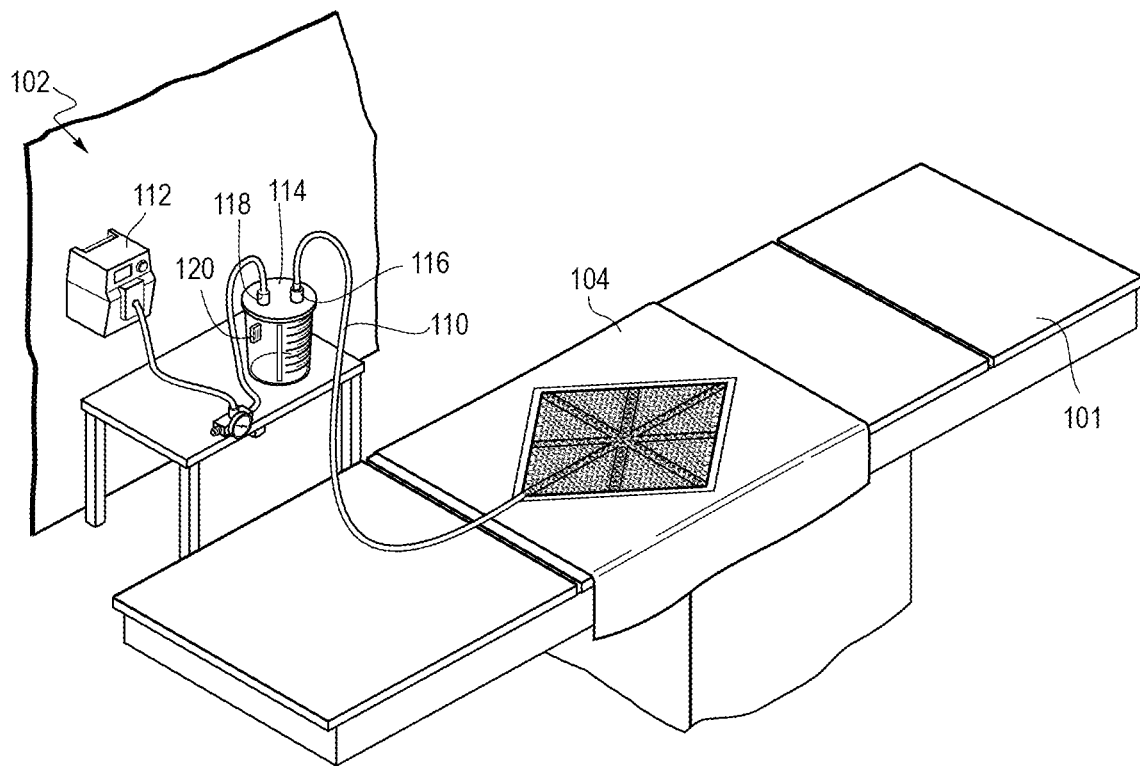
FIG. 1 is an illustration showing a vacuum system for collecting and monitoring a fluid in accordance with certain aspects of the present disclosure.
Figure 2:
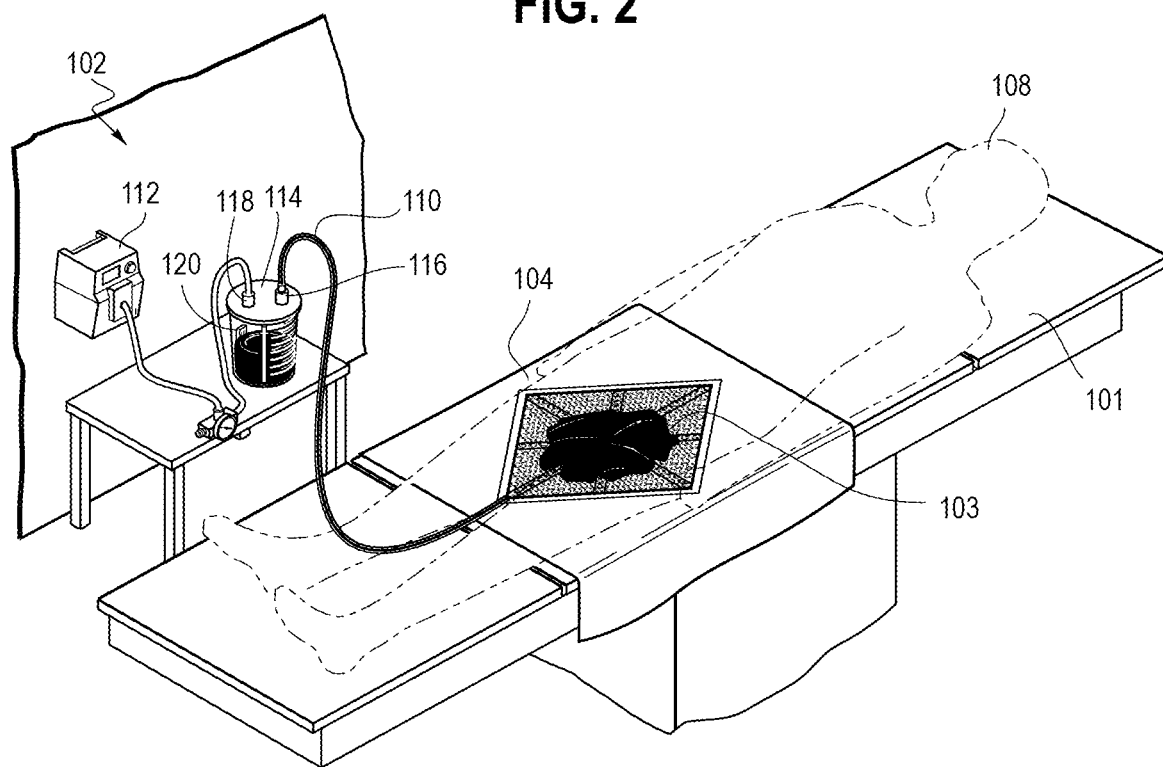
FIG. 2 is an illustration showing the vacuum system from FIG. 1 during a surgical procedure, where blood is being collected in accordance with certain aspects of the present disclosure.

FIGS. 1-2 show an example of a vacuum fluid collection system 102. The system 102 generally includes a vacuum pad 104 being utilized for the collection of blood 103 or another fluid from a patient. The vacuum pad 104 and vacuum system 102 are described herein as being designed for use in a medical setting. However, it is recognized that these devices may additionally or alternatively be used in other contexts, including settings outside of medical applications.

In the depicted embodiment, the vacuum pad 104 and/or the remainder of the vacuum system 102 may be used for any suitable medical procedure, particularly where the collection and monitoring of a body fluid originating from a patient 108 are desired. For simplicity of description, this disclosure focuses on the collection and monitoring of blood 106 from a surgical table 101 during a C-section (e.g., FIG. 2). Since some women experience moderate to severe bleeding from the uterus during a C-section, it is desirable to collect the blood as it comes from the woman's body and to remove it from the top surface of the surgical table. Further, since excess blood loss can be dangerous, it is desirable to monitor the total amount of blood lost during the procedure as well as the real-time rate of loss. The devices and methods described herein accomplish both of these features.

The vacuum system 102 may generally include the vacuum pad 104, which is configured to be placed on the surgical table 101 and beneath a patient's body 108. As discussed in greater detail below, the vacuum pad 104 may be configured for the collection of blood (or another fluid) from the patient, and may direct that blood to a vacuum hose 110 to move the blood away from the surgical table 101. In other embodiments, the vacuum pad 104 may be a portion of the surgical table 101 (e.g., providing a portion of the support for the table's top surface).

The vacuum hose 110 may ultimately be in fluid communication with a vacuum source 112. Any suitable vacuum source 112 may be used. For example, the vacuum source 112 may be a common vacuum-supply system available in many hospital settings that comply with NFPA99 design standards, where a pump within a dedicated room of the building provides a vacuum to each (or many) of the hospital rooms via vacuum plumbing. In other applications, a portable, stand-alone vacuum source 112 may be used instead.

A canister 114 may be located between the vacuum pad 104 and the vacuum source 112, as shown. The canister 114 may be configured for collecting and storing the blood as it is pulled from the vacuum pad 104. For example, an inlet 116 to the canister 114, and also a vacuum outlet 118, may be located near a top portion of the canister 114. Advantageously, once blood enters from the top of the canister 114 via the inlet 116, it falls to the bottom of the canister 114 where it remains collected and stored for the duration of the procedure.

The total blood loss from the patient 108 may directly correlate with the volume and/or mass of blood collected within the canister 114. This may be monitored visually (e.g., with graduations on a transparent surface of the canister 114) and/or electrically. For example, a sensor 120 may be included with the canister 114 for detecting a characteristic of the blood or other fluid within the canister 114. In some embodiments, the sensor 120 may be a fluid level sensor that is fixed to the canister 114. In other embodiments, the sensor 120 may alternatively or additionally be a weight/mass scale placed beneath the canister 114 such that the mass of liquid within the canister 114 is monitored. Any other suitable sensor can be alternatively or additionally included.

When coupled within a monitor/alarm system, a computer of the monitor/alarm system may be electrically connected to the sensor 120 such that the monitor/alarm system evaluates the blood collection and compare such collection to particular quantity and/or rate thresholds. If a preset threshold is met, the monitor/alarm system may provide an alert, such as by sounding a visual or audible alarm or by otherwise notifying the medical professional(s) of potential problem. The monitor/alarm system may additionally or alternatively include data collection and evaluation capabilities such that the procedure can be evaluated after the fact.

In addition to the depicted sensor 120, the canister 114 may include one or more sensors or other devices for detecting other characteristics of the blood or other fluid. For example, the system may be capable of detecting and monitoring a visual characteristic (e.g., color, a viscosity of the fluid, a conductivity of the fluid, temperature of the fluid, a salinity of the fluid, an acidity of the fluid, or any other characteristic where evaluation is desirable.

Figure 3:
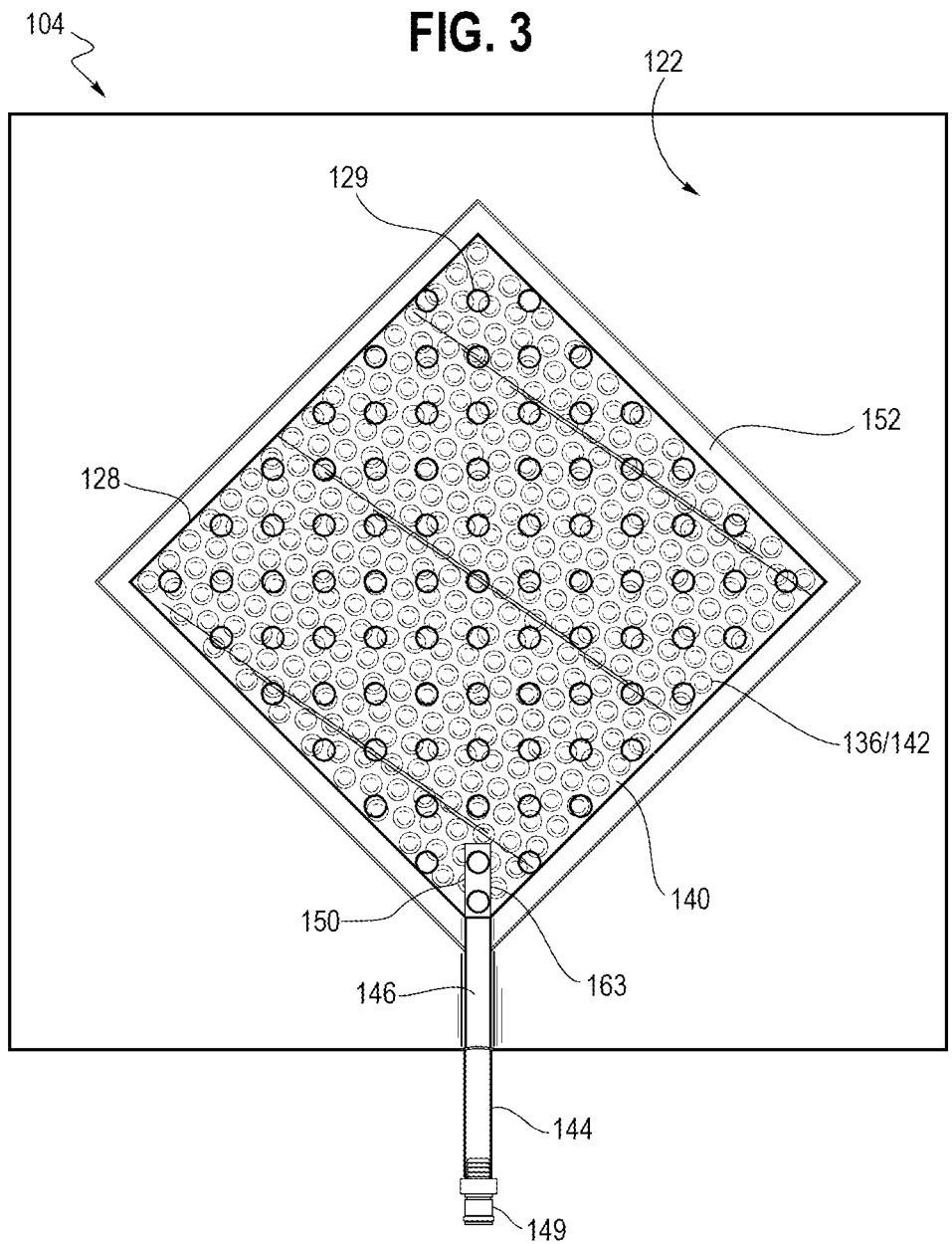
FIG. 3 is an illustration showing an isolated view of the vacuum pad from the system of FIG. 1.
Figure 4:
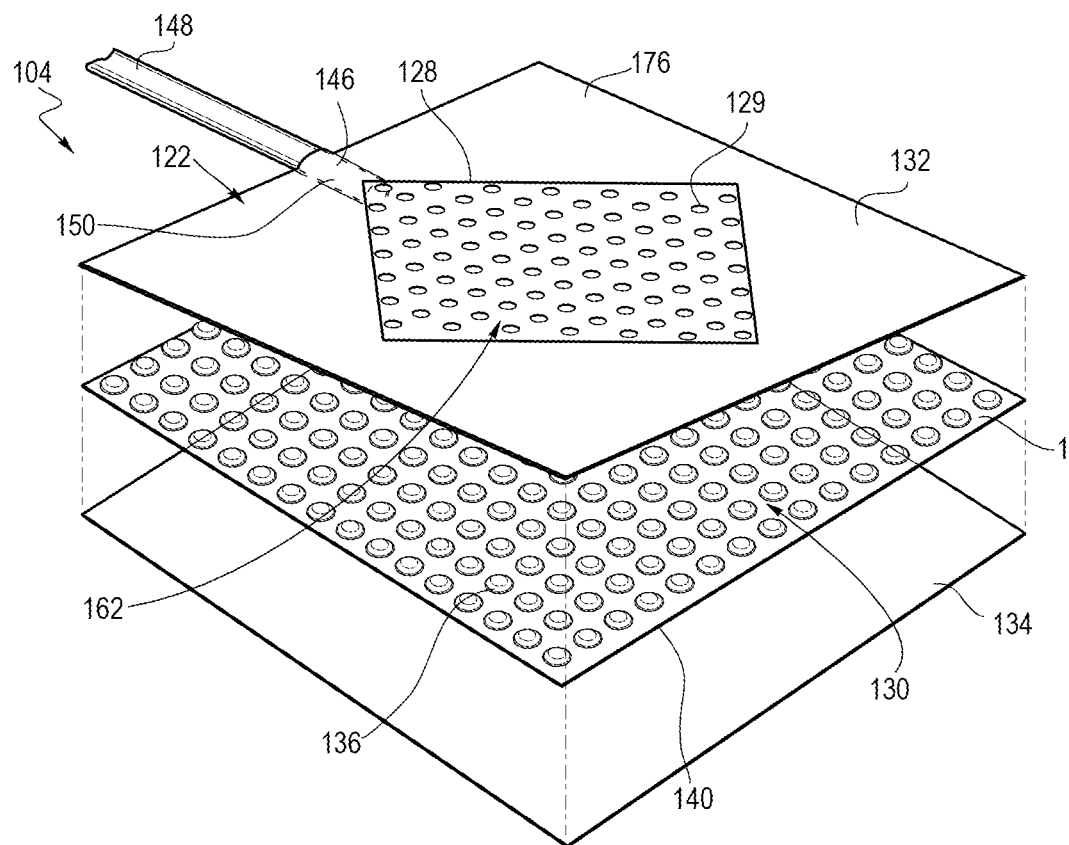
FIG. 4 is an illustration showing an exploded view of a portion of the vacuum pad from FIG. 3 having a multi-layer construction with spacers therein in accordance with certain aspects of the present disclosure.

FIGS. 3-4 show the vacuum pad 104 in isolation. During a medical procedure, the upper surface 122 may face the patient body, and the lower surface 124 may face opposite the upper surface 122 (e.g., such that the lower surface 124 may contact a surgery table). An active area 128 of the vacuum pad 104 may be surrounded by a boundary portion 176 (which is discussed in more detail below), where the active area 128 is generally sized and shaped for placement beneath a target area of the patient's body for fluid collection.

The vacuum pad 104 may be outfitted with drainage capability (and/or other fluid-control capability, such as absorption) for removing or otherwise addressing fluid that would otherwise collect on the vacuum pad's upper surface 122. For instance, the upper surface 122 of the vacuum pad 104 may include one or more holes 129 that extend to a chamber or interior space 130 within the vacuum pad 104. The interior space 130 may be defined between a top layer 132 and a bottom layer 134 (see FIG. 4). When blood collects on the upper surface 122, it flows through these holes 129 and into the interior space 130. This flow may be caused or assisted via the vacuum system discussed above.

The materials forming the top layer 132 and/or the bottom layer 134 may be any suitable material(s). For example, the top layer 132 may be formed of a hydrophobic material to ensure the vacuum pad 104 does not absorb any liquid, which may be advantageous for facilitating flow of the fluid towards the center of the vacuum pad 104. The bottom layer 134 may include a texturized, non-slip material on its bottom surface, which may ensure the vacuum pad 104 maintains proper placement relative to the surgical table, for example.

To form the interior space 130 inside the vacuum pad 104, the top layer 132 and the bottom layer 134 may be separated via one or more spacers 136. For example, spacers 136 may be included between the top layer 132 and the bottom layer 134 such that the interior space 130 is formed with a plurality of fluid flowpaths or channels that generally extend around and between the spacers 136. The spacers 136 may be formed with any suitable structure. For example, in a non-limiting exemplary embodiment, the spacers 136 may be air pockets surrounded by a membrane 140 (e.g., of a polymer) or another sealed structure. To ensure the spacers 136 maintain desirable relative positioning, the spacers 136 are optionally secured to one another and/or to at least one of the top layer 132 and the bottom layer 134 of the vacuum pad 104. For example, these air pockets 142 may be coupled together via one or more securement structures to form a spacer pad, in this case in a manner resembling (or identical to) a sheet of common bubble wrap. When the spacers 136 include the membrane layer 140, it is possible for the membrane layer 140 to act as the lower-most layer of the vacuum pad 104 (meaning the bottom layer 134 shown in FIG. 4, or alternatively the top layer 132, may be absent), but this is not required.

Forming the spacers 136 with resilient air pockets may be advantageous since such spacers may provide cushioning to the patient due to the compressibility of the air within, particularly when patient's body weight will at least partially rest upon the vacuum pad 104. While the spacers 136 may compress a certain amount, the spacers 136 will ideally retain their shape enough such that the channels 138 between the spacers 136 are not sealed off. However, since a relatively large active area 128 with many spacers 136 may be included, restriction or prevention of blood flow between certain adjacent spacers 136 in certain areas of the vacuum pad 104 may occur without substantially harming the overall function of the vacuum pad 104.

Additionally or alternatively, spacers may be included that have a different construction. For example, solid spacers formed of rubber or another compliant material may be used and may have a similar cushioning effect. In situations where compressibility is not desirable (e.g., where uninterrupted fluid passage between spacers is critical), relatively rigid spacers may be used. The spacers 136 may have any suitable size, shape, orientation, relative positioning (e.g., pattern), or the like such that blood flow, cushioning, and/or other characteristics are appropriate for a particular application. For example, the spacers 136 may be located such that they are offset relative to the holes 129 (e.g., such that they do not block the holes 129). Notably, this disclosure also covers embodiments without spacers altogether, such as an embodiment where the vacuum pad 104 includes a continuous absorbent material, where one or more tubes extending through the vacuum pad 104 render the spacers unnecessary, etc.

In the depicted embodiment, the interior space 130 between the upper top layer 132 and the bottom layer 134 may be in fluid communication with the vacuum source 112 via direct fluid communication. For example, a hollow outlet tube 144 may have an internal portion 146 that is within the interior space 130 and an external portion 148 that is outside the interior space 130. The external portion 148 of the outlet tube 144 may be connectable to the vacuum hose 110 shown in FIG. 1. Optionally, the outlet tube 144 may include a particular interface connection 149, such as threads, an O-ring, etc. where the hose 110 may be connected in a non-leaking manner.

While it is contemplated that the outlet tube 144 may simply be replaced by an extended version of the vacuum hose, a separate outlet tube 144 may be advantageous where it is desirable for the outlet tube 144 to be rigid, while the vacuum hose may be better suited as a flexible hose. For example, rigidity for the internal portion 146 of the outlet tube 144 may be important for ensuring fluid communication at the outlet of the vacuum pad 104 is not interrupted, even when under a load (e.g., the weight of the patient). By contrast, flexibility within the vacuum hose may be desirable such that the hose can be moved or otherwise manipulated throughout the room to avoid obstacles, stay clear of the surgery area, etc.

To illustrate further, the internal portion 146 of the outlet tube 144 shown in FIGS. 3-4 may include a rigid length 150 that protects the structural integrity of the outlet from the active area 128. Such a feature is particularly advantageous where the spacers 136 or other features are deformable and may otherwise have the potential for blocking/sealing off the pathway to the vacuum hose. The structure of the internal portion of the outlet tube 144 may be substantially the same as the exterior portion of the outlet tube 144, or not. For example, in some embodiments, the internal portion 146 and the external portion 148 may simply be a cylindrical-shaped tube with a uniform (and common) exterior surface. For example, a section of ⅜" diameter plastic tubing may be used without significant modification. However, in other embodiments, the internal portion 146 and the external portion 148 may be different. For example, if the internal portion 146 of the outlet tube 144 extends beneath the holes 129, it may have a matching set of openings/holes (or another permeable structure) that allow direct flow from the upper surface 122, through the holes 129, and into the outlet tube 144. By contrast, the external portion 148 of the outlet tube 144 should remain fluid-impermeable so it does not leak.

Figure 5:
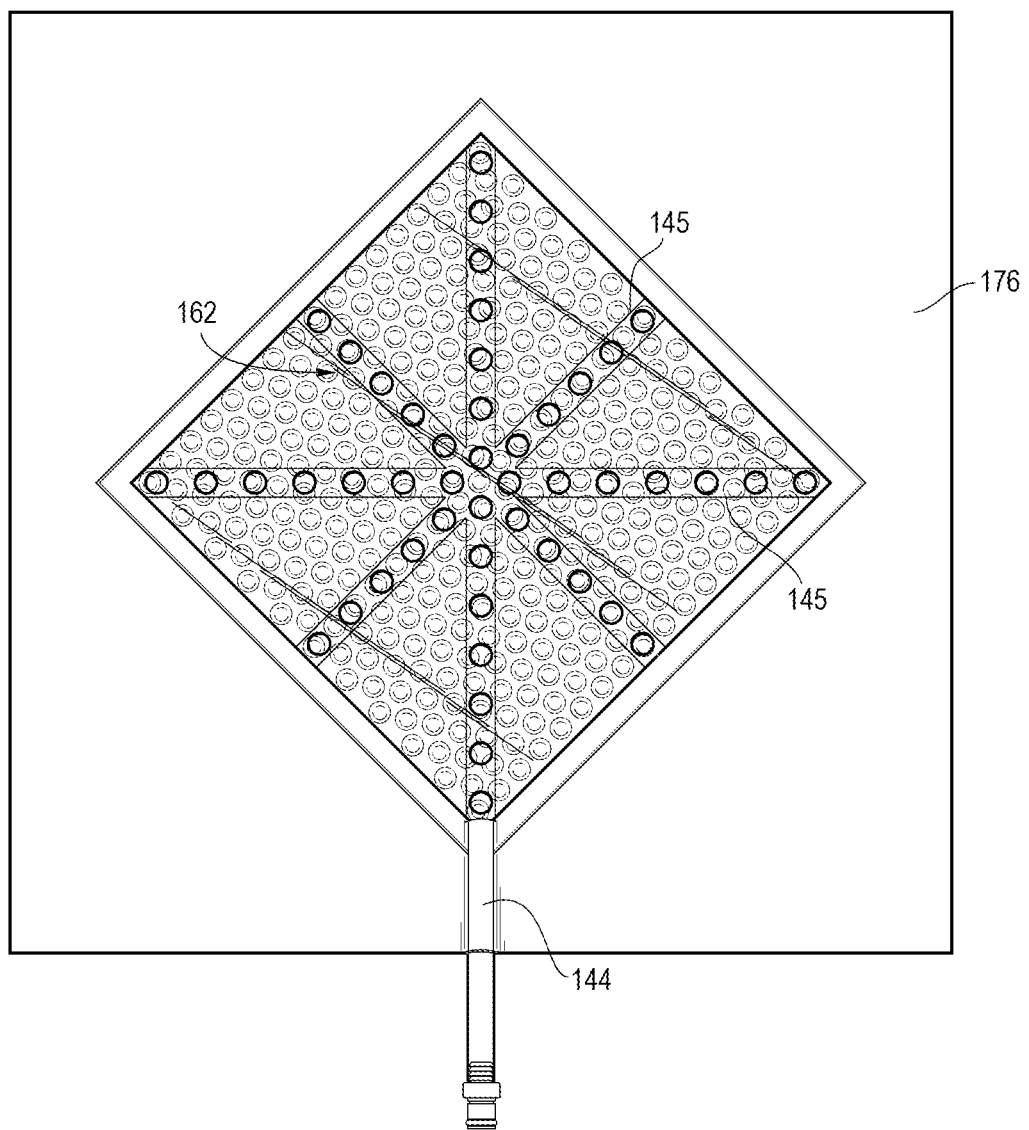
FIG. 5 is an illustration showing a second embodiment of a vacuum pad having a tube extending through an interior space in accordance with certain aspects of the present disclosure.
Figure 6:
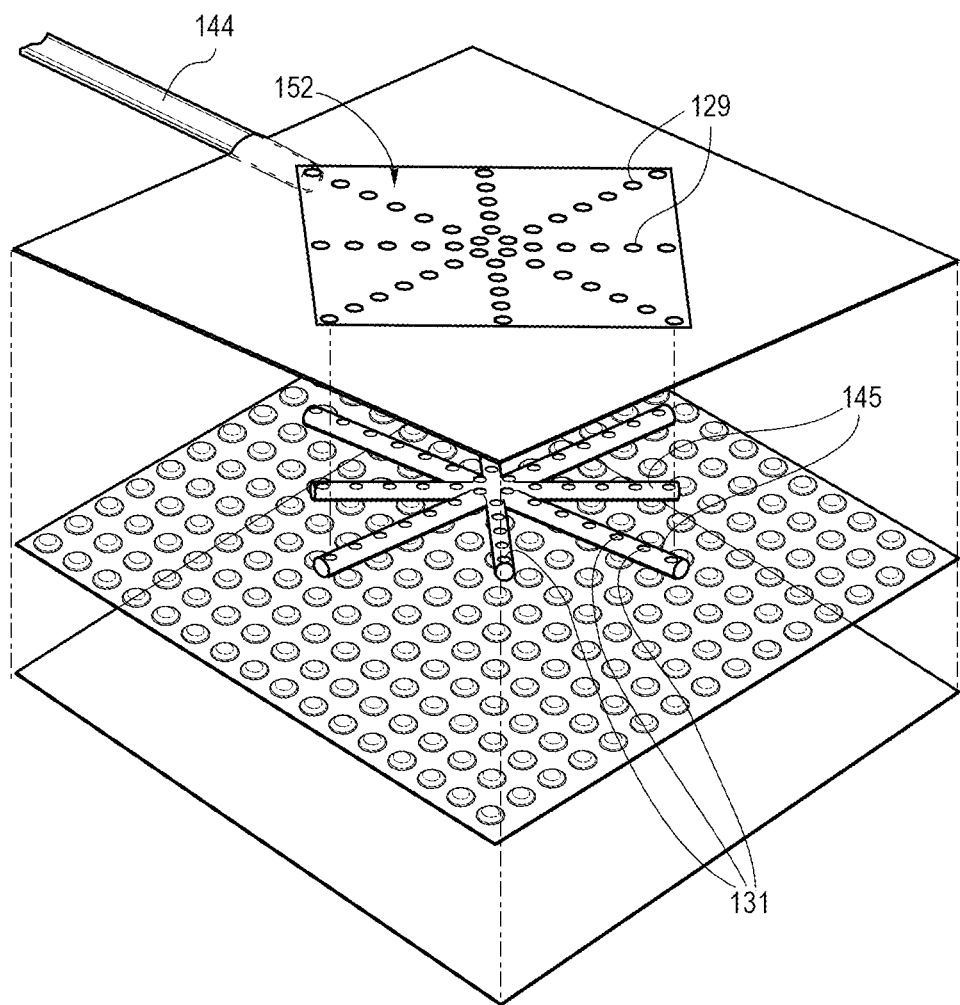
FIG. 6 is an illustration showing an exploded view of a portion of the vacuum pad from FIG. 5 having a multi-layer construction with spacers therein in accordance with certain aspects of the present disclosure.

While the outlet tube 144 terminates soon after it enters the interior space 130 in FIG. 3, it may extend further in other embodiments, for example to roughly the center, or substantially across the active area 128, etc. To illustrate, referring to FIGS. 5-6, the outlet tube 144 may have one or more bifurcations where different branches 145 go different directions within the interior space 130. If the holes 129 are arranged in a particular pattern (for reasons discussed below in more detail), the outlet tube 144 may be substantially coextensive this pattern, for example, and it may include a set of holes 131 that are generally coextensive with the holes 129. Such a design may be advantageous for providing enhanced support for the interior space 130 where fluid flow rate may be critical. As mentioned above, such an embodiment may lack the need for spacers, but the spacers 136 remain included in the depicted embodiment for enhanced flow capability through the interior space 130 of the vacuum pad 104. To provide the ability for fluid to enter the outlet tube 144, the outlet tube 144 may include one or more openings, be formed of a porous material (e.g., a textile, a netting, etc.), or the like such that blood can flow into the outlet tube 144.

Figure 7:
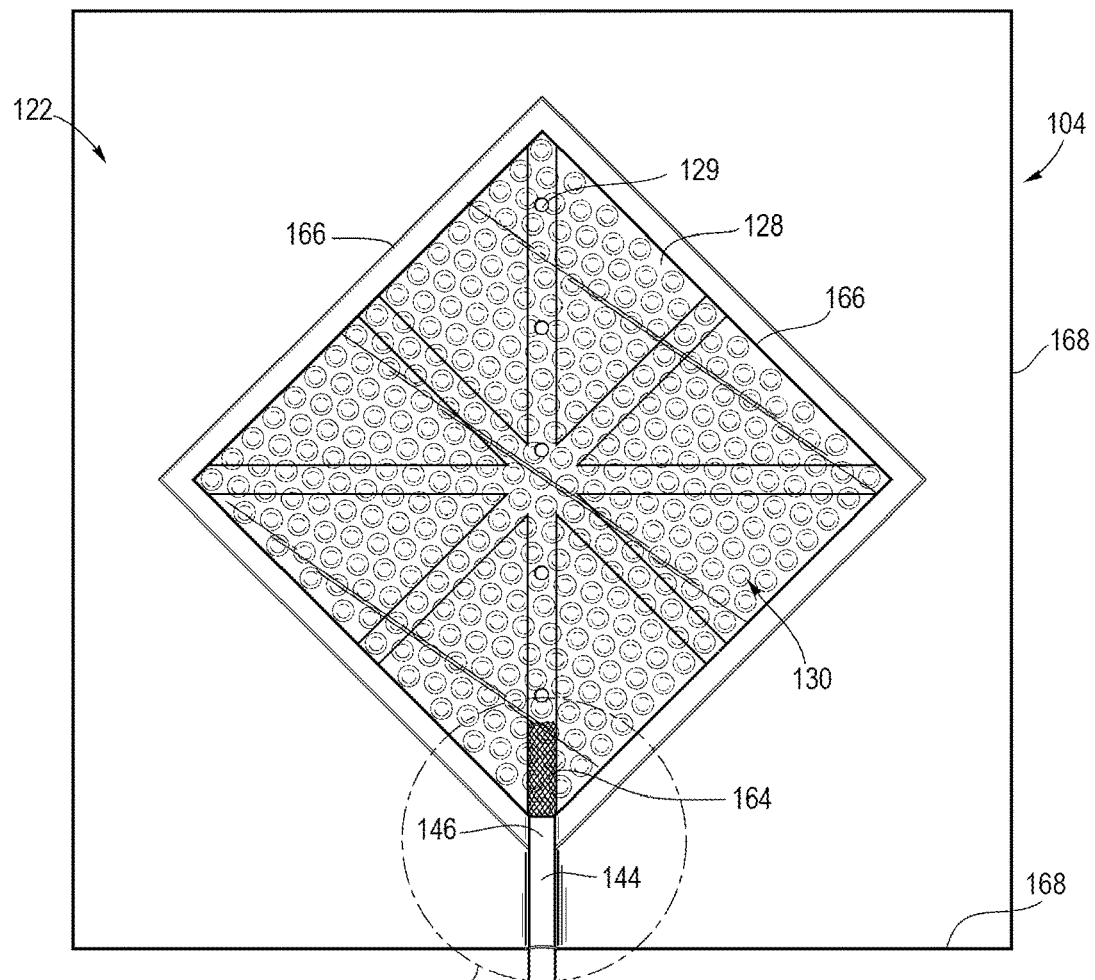
FIG. 7 is an illustration showing a third embodiment of a vacuum pad having a support structure extending from an outlet tube in accordance with certain aspects of the present disclosure.
Figure 8:
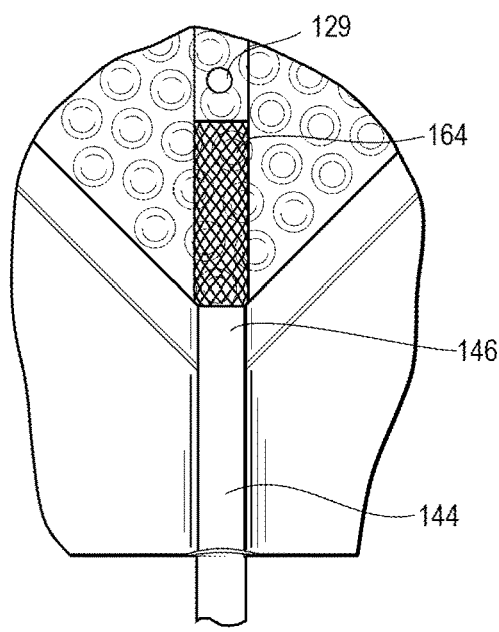
FIG. 8 is an illustration showing a magnified view detailing the support structure from the embodiment of FIG. 7.

In another example, and as shown by FIGS. 7-8, one or more support structures 164 may extend from a terminal end of the outlet tube 144. As shown, the support structure 164 may include a set of protrusions, a netted/porous sleeve, or any other suitable structure that provides structural integrity to the interior space 130 at a location adjacent to the outlet tube 144. Such support structures may also/alternatively be located at other places. E.g., in a manner similar to the embodiment discussed above with reference to FIGS. 5-6, this support structure 164 may extend along a portion of, or the entirety of, a drainage pattern of the vacuum pad 104.

The active area 128 of the vacuum pad 104 may have a variety of shapes and sizes, depending on the preferred application (e.g., C-section vs. other applications), size of the patient, strength of the vacuum source, manufacturing constraints, etc. For example, the embodiments of FIGS. 1-8 each have a generally-square active area 128. While any suitable size may be used for a particular set of circumstances, the active area 128 may generally have an area of between about 3 square feet to about 0.5 square feet, such as about 1 square foot in an embodiment particularly designed for use during C-sections. The holes 129 may also be intentionally sized for particular fluid and vacuum characteristics. In the above-mentioned embodiment for C-sections, ideal hole diameter sizes range from about 0.020 inches to about 0.060 inches, such as about 0.040 inches. Optionally, the holes 129 may be sized to filter out certain objects (e.g., blood clots) such that the vacuum hose remains clog-free.

Notably, the performance of the device may be heavily influenced by the size of the active area 128, as well as the size, pattern, and number of holes 129. For example, during testing and using a wall vacuum source in accordance with the hospital standards noted above, a 12" by 12" active area having a star hole pattern (discussed below) with hole sizes mentioned above, the device provided consistent, high-performing results. In particular, the device proved capable of handling flow rates onto the upper surface 122 of up to 500 mL/min of blood without significant leakage or fluid loss. Using a 250 mL/min test flow, less than 15 mL leaked over the first 600 mL of fluid drawn into the canister.

When a square active area 128 is included, it may be advantageous for the edges 166 of the square to be angled relative to terminal edges 168 of the vacuum pad 104. For example, since it may be advantageous for the vacuum pad 104 to be limited in size, angling the square in this manner may provide enhanced "catching" ability due to a more advantageous orientation relative to the surgical site and/or target area of the patient's body.

Figure 9:
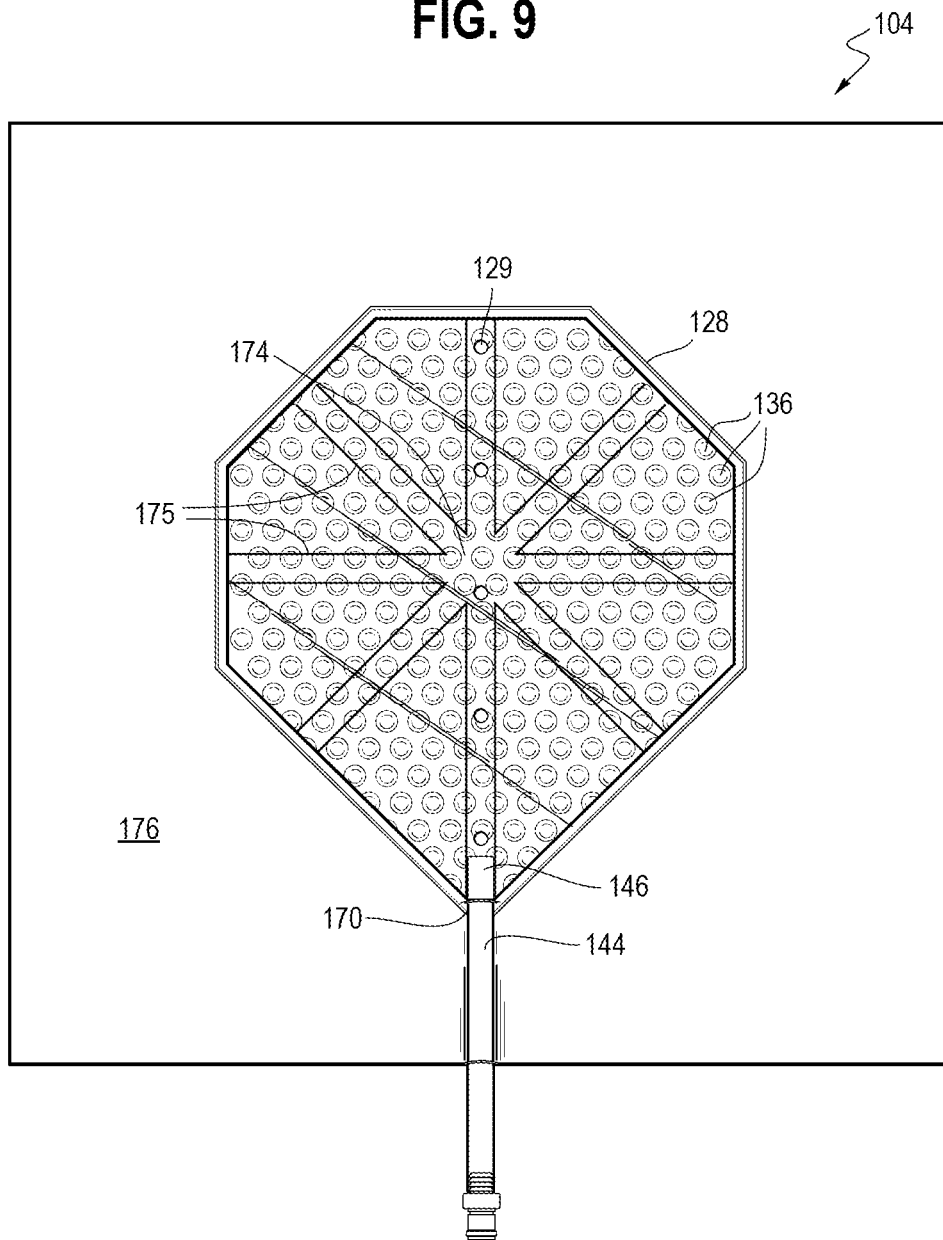
FIG. 9 is an illustration showing a fourth embodiment of a vacuum pad having a polygon active area and star opening pattern in accordance with certain aspects of the present disclosure.
Figure 10:
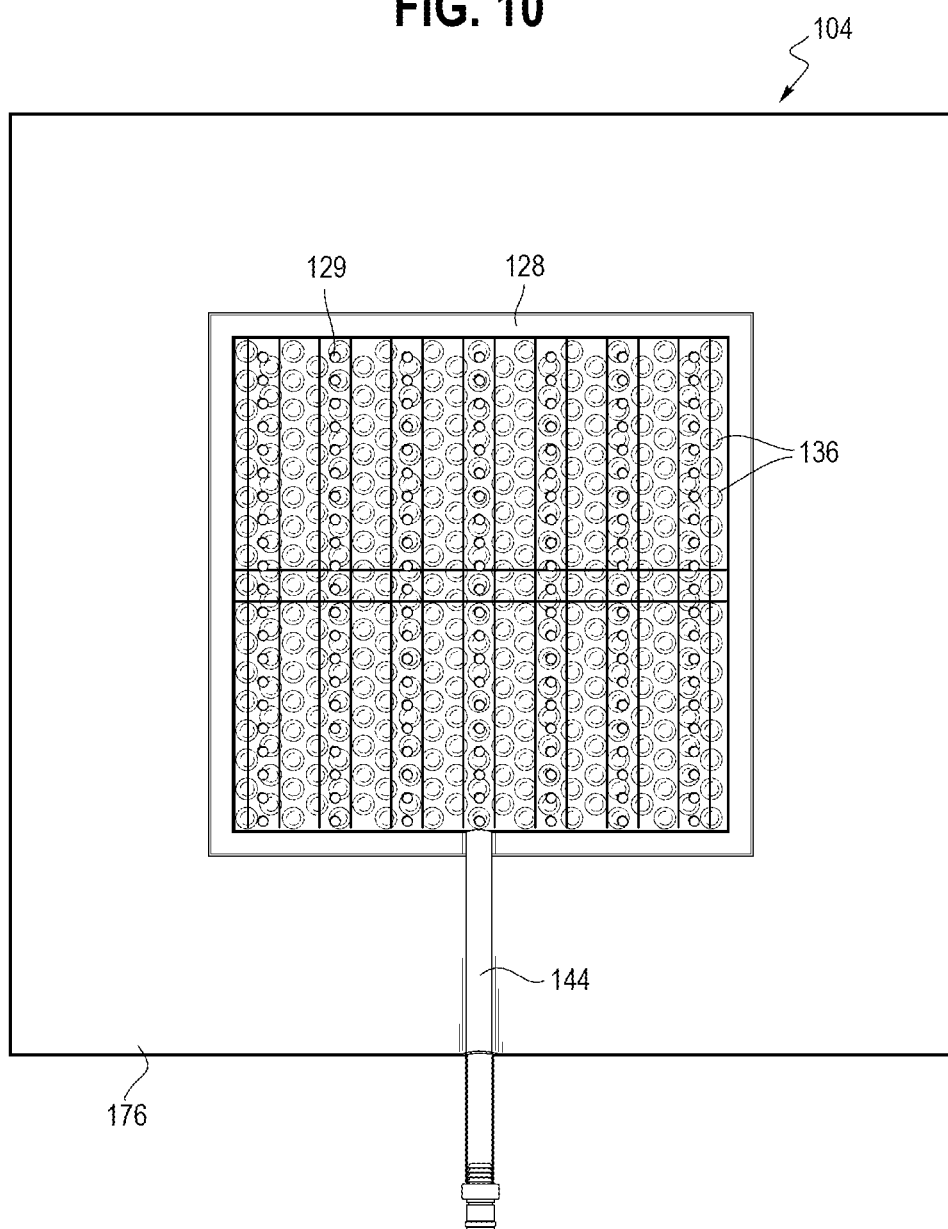
FIG. 10 is an illustration showing a fifth embodiment of a vacuum pad having a square active area and grid opening pattern in accordance with certain aspects of the present disclosure.

Other shapes and/or sizes of the active area 128 are additionally or alternatively contemplated. For example, as shown in FIG. 9, an irregular polygon (in this case an octagon) may be included with the outlet tube 144 entering at the sharpest vertex 170. FIG. 10 depicts a standard square that is not angled (in contrast to the device(s) of FIG. 1-8). Many other variations may alternatively be used. For instance, the shape of the active area 128 may be specifically designed or selected for a particular orientation and/or placement relative to the patient, and optimal shape, orientation, and/or size may vary depending on the particular procedure to be performed, size of the operating table, vacuum strength, surgeon preference, etc.

The size and/or shape of the active area 128 may also depend on the desired size of the holes 129. To illustrate, the active area 128 may be relatively larger while the hole size (or number of openings) may be relatively smaller, which may allow for a larger active area 128 without unduly sacrificing per-unit-area vacuum strength. The inverse may also be true: the size of the active area 128 may be relatively small, but the opening size (and/or number of holes 129) may be relatively large per unit area of the active area 128 such that a sufficient vacuum strength per-unit-area is possible.

The arrangement of the holes 129 may also affect the performance of the vacuum pad 104 performance, and the inventors conceived of several specific hole arrangements that improve the capabilities of the device. In particular, and as shown in each of the embodiments of FIGS. 5-9, the holes 129, the holes 129 may generally be arranged in a star pattern. Referring to FIG. 9, the star pattern may include a central area 174 along with a set of branches 175 that each extend radially outwardly from the central area 174. While any number of holes 129 may be located in each branch 175, in certain non-limiting embodiments, the holes 129 are spaced apart within the branches 175 such that about 0.3 inches to about 0.5 inches of space is located between adjacent holes 129 (and a similar spacing may be used with other patterns, for example). At least one of the branches 175 may generally align with the internal portion 146 of the outlet tube 144, which may reduce internal pressure loss as the blood moves into the outlet tube 144. While the spacers 136 are generally located throughout the active area 128, in other embodiments the spacers 136 may be concentrated beneath the locations of the holes, for example.

Other drainage patterns are also contemplated. FIG. 10 shows the holes 129 are generally placed in a grid pattern, for example, with gridlines generally parallel to the lines of the boundaries of the active area 128. FIG. 3-4, on the other hand, show a generally uniform distribution of the holes 129. May other options are also available.

Figure 11:
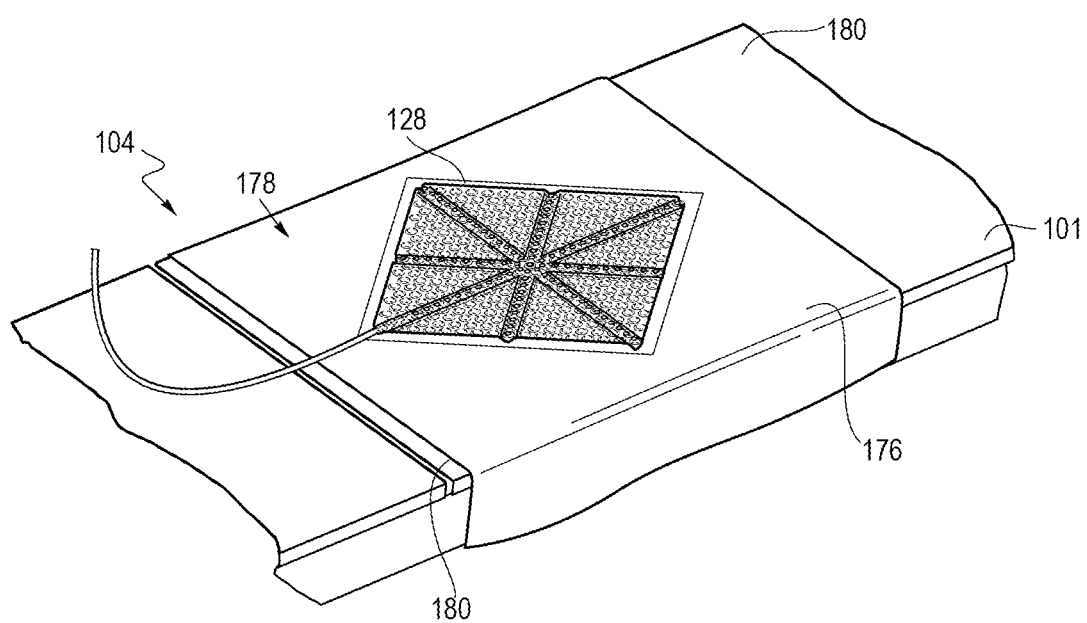
FIG. 11 is an illustration showing a vacuum pad having an active area surrounded by a boundary area in accordance with certain aspects of the present disclosure.

Referring to FIG. 11, the vacuum pad 104 may include the defined active area 128 that is at least partially surrounded by a boundary portion 176. Optionally, the boundary portion 176 may include a construction that is substantially different than a construction of the active area 128. For example, the boundary portion 176 may generally lack the channels, spacers, and/or other features included in the active area 128 since the boundary portion 176 may not be designed to drain the fluid, although the boundary portion 176 may be configured to direct the fluid towards the active area 128 in some embodiments. For example, the boundary portion 176 may include a low-friction, water-repellant material to facilitate flow towards the center of the vacuum pad 104.

The boundary portion 176 may further include a rigidity that is greater relative to a rigidity of at least the top layer of the active area 128. For example, the boundary portion 176 may include a wood, rigid polymer/plastic, metal, or other material that causes the boundary portion 176 to retain its shape. This may be the case even when the boundary portion 176 is not placed on a surgical table. In fact, in some embodiments, the boundary portion 176 may form a portion of an upper surface 178 of the surgical table, and it is contemplated that the top of the boundary portion 176 may include cushioning and/or other features appropriate for supporting the patient's body. In certain instances, the boundary portion 176 may have a strength and rigidity sufficient such that the vacuum pad 104 may be moved while supporting the patient's body, thus having the capability to act as a transport surface for moving the patient from one place to another. When this is the case, certain indicators and/or handles may be included to indicate where lifting force should be applied. As depicted, the boundary portion 176 may be generally adjacent and co-planar to a separate support surface structure 180 of the surgical table 101, but this is not required.

Figure 12:
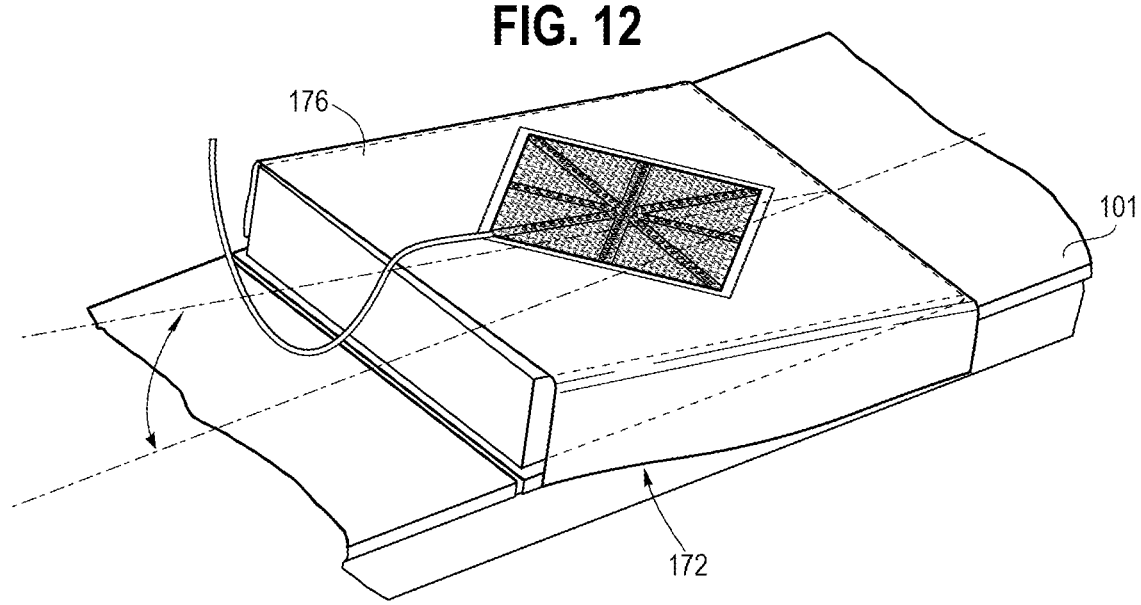
FIG. 12 is an illustration showing a vacuum pad having an active area surrounded by a barrier in accordance with certain aspects of the present disclosure.

FIG. 12 shows an embodiment where the boundary portion 176 is sloped relative to the surgical table 101. The slope may be caused by an angled surface 172 located on the bottom of the boundary portion 176, which may rest on a flat surface.

Figure 13:
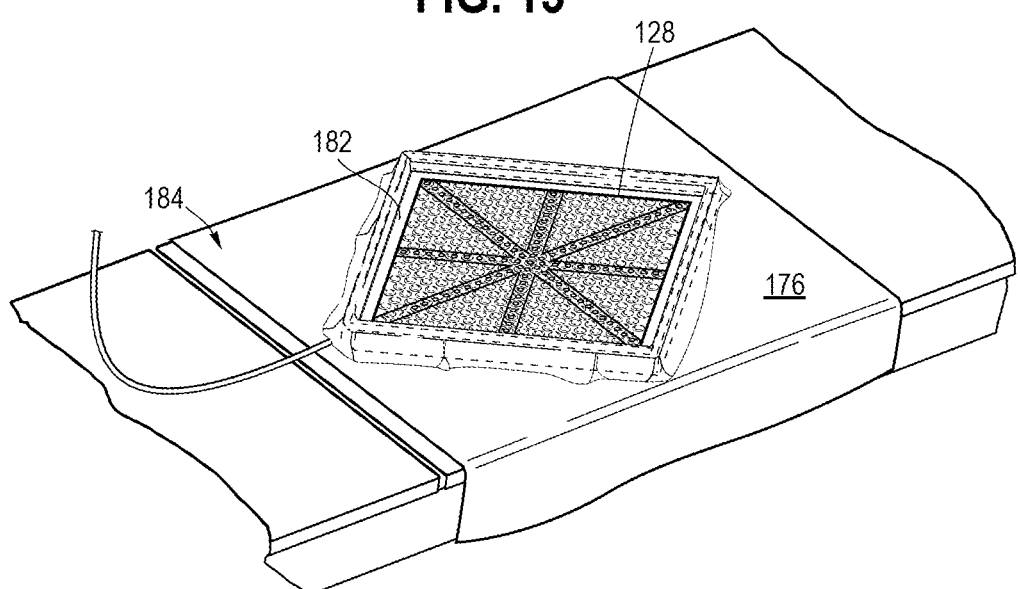
FIG. 13 is an illustration showing a vacuum pad having a sloped surface for directing a fluid in a certain direction in accordance with certain aspects of the present disclosure.

As shown in FIG. 13, certain embodiments may include a raised barrier 182 that forms an interface between the active area 128 and the boundary portion 176 of the vacuum pad 104. The barrier 182 may extend from a top surface 184 of the boundary portion 176 and/or the active area 128 such that fluid collected on the active area 128 remains in place until it can be pulled away by the vacuum source. For example, in certain situations, fluid loss from the patient's body may happen at a faster rate than the active area 128 can handle in real-time, and thus the barrier 182 may form a receptacle for storing this fluid for a period of time. This may also advantageously trap blood prior to activation of the vacuum source and/or connecting the vacuum pad 104 to the hose 110.

As an alternative to the raised barrier 182, a different or additional structure may be included that accomplishes a similar function. For example, the active area 128 may be depressed relative to the top surface 184 of the boundary portion 176, for example. In other embodiments, the overall slope of the top surface 184 of the boundary area (and perhaps also the active area 128) may slope towards the center of the device. Such a slope may be caused by a particular construction causing a "default" slope (e.g., even when no patient is resting on the device), and/or the weight of the patient may create such a slope when the device is designed to conform/compress under when experiencing a load.

Figure 14:
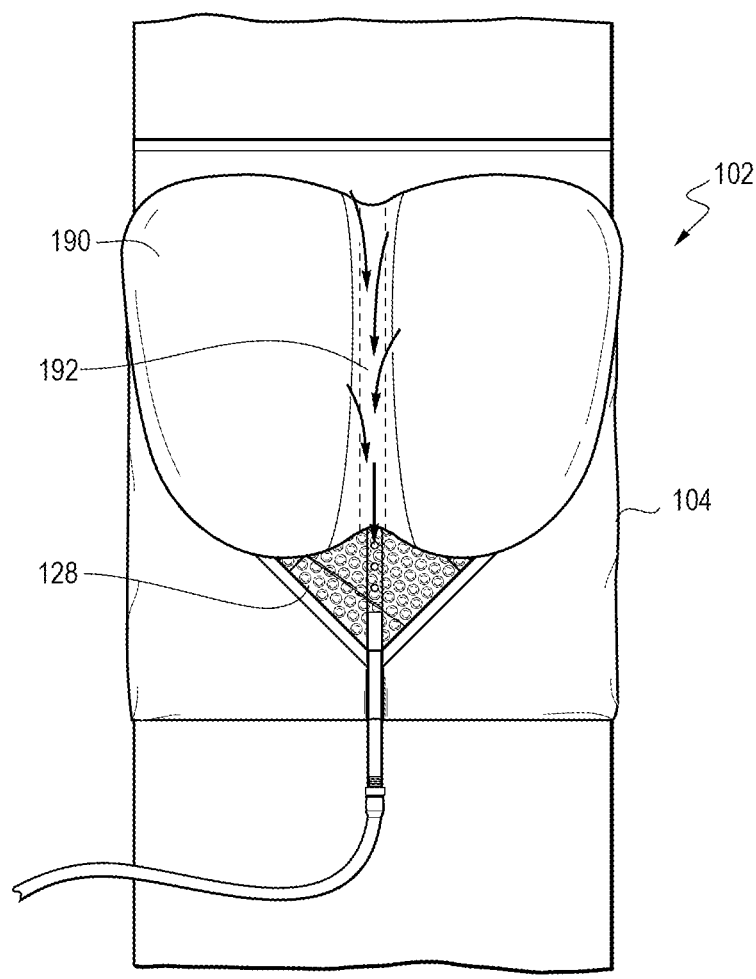
FIG. 14 is an illustration showing a vacuum pad being coupled to a funnel jig for directing fluid towards the vacuum pad in accordance with certain aspects of the present disclosure.
Figure 15A:
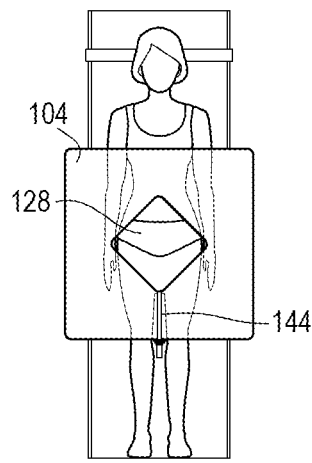
FIGS. 15A-15D are illustrations showing a vacuum pad having an outlet tube extending from different locations in accordance with certain aspects of the present disclosure.
Figure 15B:
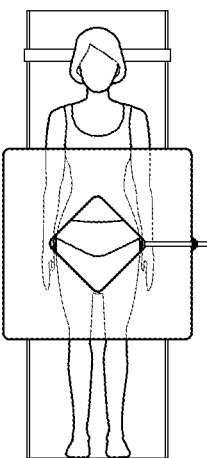
Figure 15C:
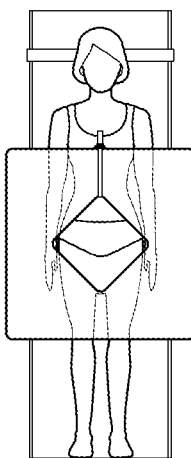
Figure 15D:
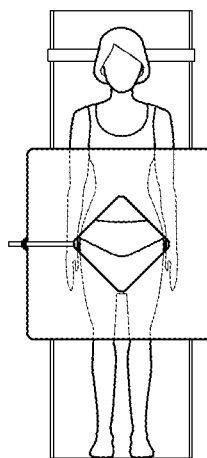
Figure 16A:
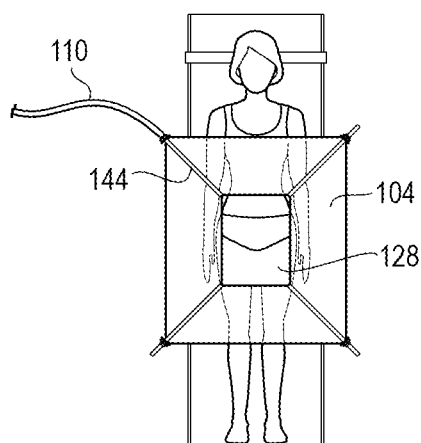
FIGS. 16A-16B are illustrations showing a vacuum pad having multiple outlet tubes in accordance with certain aspects of the present disclosure.
Figure 16B:
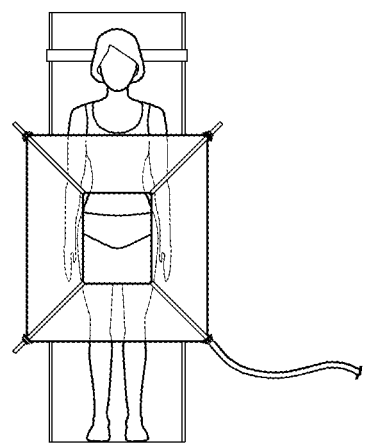
Figure 17A:
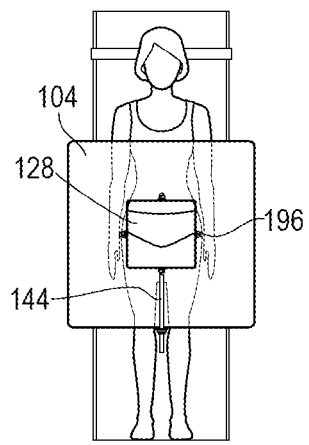
FIGS. 17A-17D are illustrations showing a vacuum pad having multiple ports for receiving an outlet tube in accordance with certain aspects of the present disclosure.
Figure 17B:
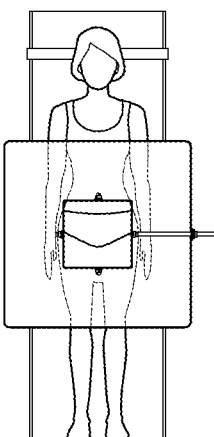
Figure 17C:
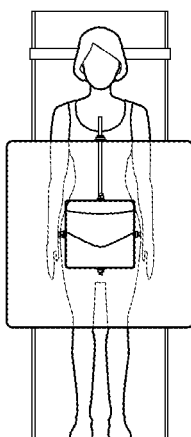
Figure 17D:
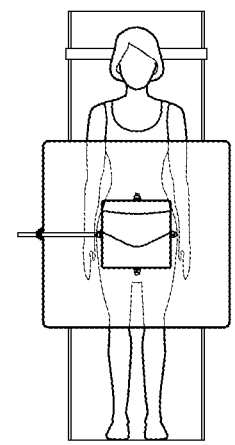

Referring to FIG. 14, the system 102 may optionally include a jig 190, which may be configured to direct fluid towards the active area 128 of the vacuum pad 104. For example, the jig 190 of FIG. 14 may generally fit under the sacrum and/or ischial tuberosities of a patient when used for a C-section. A central channel 192 of the jig 190 may be generally sloped towards the active area 128 such that, if and when blood flows onto the jig 190, it is directed towards the active area 128 for collection in the manner discussed above. The jig 190 may be fixed to the vacuum pad 104, but this is not required. Similarly, the jig 190 may be secured to the surgical table, or it may be freely movable.

FIGS. 15A-15D show several potential locations where the outlet tube 144 may enter the active area 128 of the vacuum pad 104. For example, in each of FIGS. 14A-14D, the location of the outlet tube 144 may enter the active drainage area where two or more edges of the active area 126 meet at a corner or vertex 170. Advantageously, including the outlet tube 144 at a vertex may create a funnel effect within the interior space of the active area 128 as blood moves towards the outlet tube 144. In the embodiment of FIGS. 15A-15D, the vacuum pad 104 may be rotated such that the outlet tube 144 is in an accessible and convenient location for connection to the vacuum tube. That is, the vacuum pad 104 may work in several different orientations such that it can be placed under a patient body in a variety of ways.

In another embodiment (shown in FIGS. 15A-15B), the vacuum pad 104 may include multiple outlet tubes 144, and/or other outlet structures, such that a particular outlet structure may be chosen and connected to the vacuum hose 110 (e.g., while others go unused). In such embodiments, it may be desirable for the non-used outlet tubes to include a seal, cap, etc. such that the vacuum within the interior space is not negatively influenced. Additionally or alternatively, multiple vacuum hoses may be coupled to multiple outlets, and/or an outlet may be used as a tap for collection of a body fluid directly from the vacuum pad 104.

FIG. 17 includes yet another embodiment where the outlet tubes 144 may be inserted into one or more ports 196. In other words, the outlet tube 144 may be connectable and disconnectable from the remainder of the vacuum pad 104 at different locations. Advantageously, when preparing for use, the vacuum pad 104 may be placed on a surgery table in a desired location without needing to account for where the outlet tube 144 or hose will be located, which may reduce the need for perfect placement (particularly helpful in emergency situations). The outlet tube 144 can then be connected in a variety of locations, even after the patient is resting on the device.

While various embodiments have been described, it will be apparent to those of ordinary skill in the art that many more embodiments and implementations are possible. Accordingly, the embodiments described herein are examples, not the only possible embodiments and implementations.

Having described various aspects of the subject matter above, additional disclosure is provided below that may be consistent with the claims originally filed with this disclosure. In describing this additional subject matter, reference may be made to the previously described figures. Any of the following aspects may be combined, where compatible.

A first aspect includes a vacuum pad. The vacuum pad may include a top layer forming a top surface of the vacuum pad; a bottom layer forming a bottom surface of the vacuum pad; and a plurality of spacers located between the top layer and the bottom layer such that an interior space is formed between the top layer and the bottom layer, the interior space having at least one channel extending around at least one spacer of the plurality of spacers; and an outlet tube in fluid communication with the interior space. The top layer may include a plurality of holes such that the vacuum pad is configured to cause a fluid collecting on the top surface of the vacuum pad to flow through the holes, into the interior space, and to the outlet tube.

A second aspect includes the vacuum pad from the aspect 1, where the vacuum pad of the first aspect may have the set of spacers of the plurality of spacers including air pockets.

A third aspect includes the vacuum pad from any of aspects 1-2, where the bottom layer of the vacuum pad of the first aspect may include a spacer pad that at least partially forms the spacers.

A fourth aspect includes the vacuum pad from any of aspects 1-3, where the plurality of openings forms a star arrangement having a central area with a plurality of branches extending radially outward therefrom.

A fifth aspect includes the vacuum pad from any of aspects 1-4, where the outlet tube includes a rigid internal portion that extends along a drainage pattern, the drainage pattern including at least a portion of the holes in the top layer.

A sixth aspect includes the vacuum pad from any of aspects 1-5, where the outlet tube enters an active area of the top layer at a vertex of the active area.

A seventh aspect includes the vacuum pad from any of aspects 1-6 where an internal portion of the outlet tube includes a permeable structure for enhancing fluid flow into the internal portion, and where an external portion of the outlet tube includes a impermeable structure for preventing leaks at a location outside the interior space of the vacuum pad.

An eighth aspect includes the vacuum pad from any of aspects 1-6, where a permeable support structure extends from the outlet tube for protecting fluid communication at a location adjacent to the outlet tube.

A ninth aspect includes the vacuum pad from any of aspects 1-8, where an active area of the vacuum pad includes the spacers, and where the vacuum pad further comprises a boundary portion at least partially surrounding the active area, the boundary portion having a construction that is different than a construction of the active area.

A tenth aspect includes vacuum pad from any of aspects 1-9, where the boundary portion includes a rigidity that is greater than a rigidity of the top layer of the active area.

An eleventh aspect includes the vacuum pad from aspect 9, where the boundary portion includes at least one sloped surface for causing a fluid to flow towards the active area when fluid collects on the boundary portion.

An twelfth aspect includes the vacuum pad from any of aspects 9-10, further including a barrier located between the boundary portion and the active area, the boundary portion protruding upwards relative to the top surface of the active area.

A thirteenth aspect includes another embodiment of a vacuum pad. The vacuum pad may include an active area having a permeable top layer and a bottom layer such that an interior space is formed between the top layer and the bottom layer; a boundary portion surrounding the active area, the boundary portion having an impermeable top surface; and an outlet configured to couple to a vacuum source such that fluid collected on the active area is removed from the interior space towards the vacuum source.

A fourteenth aspect includes the vacuum pad aspect 13, where the boundary portion includes a sloped surface for directing the fluid towards the active area.

A fifteenth aspect includes the vacuum pad from any of aspects 13-14, where the boundary portion includes a first rectangle formed by its outer perimeter, where the active area includes a second rectangle formed by its outer perimeter, and where the first rectangle is angled relative to the second rectangle.

A sixteenth aspect includes the vacuum pad from any of aspects 13-15, where the boundary portion is configured to at least partially form a top surface of a surgical table.

A seventeenth aspect includes the vacuum pad from any of aspects 13-16, further including a fixture having a sloped surface for directing the fluid towards the active area.

An eighteenth aspect includes a vacuum system. The vacuum system may include the following: a vacuum pad for collecting a fluid flowing onto a top surface of the vacuum pad, where the vacuum pad includes a permeable top layer, a bottom layer, and a plurality of spacers located between the top layer and the bottom layer; and a canister for storing a fluid collected by the vacuum pad, where the vacuum pad includes an outlet configured for securement to a first end of a vacuum hose, and where the canister includes an inlet configured for securement to a second end of the vacuum hose such that the vacuum hose directs the fluid collected by the vacuum pad to the canister.

A nineteenth aspect includes the vacuum system of aspect 18, where the canister is coupled to a sensor for detecting a fluid level within the canister.

A twentieth aspect includes the vacuum system of any of aspects 18-19, further including a vacuum source, where the vacuum source, the canister, the vacuum hose, and the vacuum pad are connected in series.

Any of the above-discussed aspects may be combined, where suitable.

We claim:

1. A vacuum pad, comprising:
    a top layer at least partially forming a top surface of the vacuum pad;
    a bottom layer at least partially forming a bottom surface of the vacuum pad;
    a plurality of spacers located between the top layer and the bottom layer such that an interior space is located between the top layer and the bottom layer, the interior space having at least one channel extending around at least one spacer of the plurality of spacers; and
    an outlet tube in fluid communication with the interior space and having an internal portion that extends between the top layer and the bottom layer,
    wherein the top layer includes a plurality of holes such that the vacuum pad is configured to cause a fluid collecting on the top surface of the vacuum pad to flow through the holes, into the interior space, and to the outlet tube,
    wherein a raised barrier entirely surrounds the plurality of holes and the plurality of spacers, the raised barrier being elevated relative to the plurality of holes and a flat boundary portion and configured to collect the fluid over the plurality of holes, and
    wherein the boundary portion has an impermeable top surface entirely surrounding the raised barrier and extending outward therefrom.

2. The vacuum pad of claim 1, wherein at least a set of spacers of the plurality of spacers includes air pockets.

3. The vacuum pad of claim 1, wherein the bottom layer includes a spacer pad that at least partially forms the plurality of spacers.

4. The vacuum pad of claim 1, wherein the plurality of holes has an arrangement including a plurality of branches extending radially outward from a single area.

5. The vacuum pad of claim 1 wherein the internal portion of the outlet tube extends at least partially along a drainage pattern, the drainage pattern including at least a portion of the plurality of holes in the top layer.

6. The vacuum pad of claim 1, wherein the outlet tube enters the interior space at a vertex of an active area.

7. The vacuum pad of claim 1, wherein the internal portion of the outlet tube is at least partially permeable, and wherein an external portion of the outlet tube is impermeable.

8. The vacuum pad of claim 1, wherein the internal portion of the outlet tube includes a permeable support structure at a location adjacent to where the outlet tube enters the interior space.

9. The vacuum pad of claim 1, wherein an active area of the vacuum pad includes an area of at least one of the plurality of spacers, and wherein the boundary portion has a construction that is different than a construction of the active area.

10. The vacuum pad of claim 9, wherein the boundary portion includes a rigidity that is greater than a rigidity of the top layer at least in the active area.

11. The vacuum pad of claim 1, wherein the raised barrier includes at least one sloped surface configured for causing the fluid to flow towards the active area when the fluid collects on the boundary portion.

12. The vacuum pad of claim 1, wherein an inner perimeter of the raised barrier is angled relative an outer perimeter of the boundary portion.

13. A vacuum pad, comprising:
    an active area having a permeable top layer and a bottom layer such that an interior space is located between the permeable top layer and the bottom layer;
    a boundary portion entirely surrounding a perimeter of the active area, the boundary portion having an impermeable top surface, an outer perimeter, and a raised portion relative to the active area; and
    an outlet configured to couple to a vacuum source such that a fluid collected on the active area is removed from the interior space towards the vacuum source,
    wherein the perimeter of the active area is angled relative to the outer perimeter of the boundary portion.

14. The vacuum pad of claim 13, wherein the raised portion includes a sloped surface configured for directing the fluid towards the active area.

15. The vacuum pad of claim 13, wherein the boundary portion includes a first quadrangle formed by the outer perimeter of the boundary portion, wherein the active area includes a second quadrangle formed by the perimeter of the active area, and wherein the first quadrangle is angled relative to the second quadrangle.

16. The vacuum pad of claim 13, wherein the boundary portion is configured to at least partially form a top surface of a surgical table.

17. The vacuum pad of claim 13, wherein the raised portion is a raised barrier protruding upward relative to the active area and a flat portion of the boundary portion that extends outward from the raised portion, the raised barrier being configured for confining the fluid towards the active area.

18. A vacuum system, comprising:
    a vacuum pad for collecting a fluid flowing onto a top surface of the vacuum pad, wherein the vacuum pad includes a permeable area of a top layer, a bottom layer, and a plurality of spacers located between the top layer and the bottom layer; and
    a canister for storing a fluid collected by the vacuum pad, wherein an impermeable boundary portion includes a flat section extending outward from and entirely surrounding an elevated section, the elevated section protruding upwards relative to the permeable area of the top layer and the flat section,
    wherein the elevated section entirely surrounds the permeable area of the top layer,
    wherein the vacuum pad includes an outlet configured for securement to a first end of a vacuum hose, and
    wherein the canister includes an inlet configured for securement to a second end of the vacuum hose such that the vacuum hose directs the fluid collected by the vacuum pad to the canister.

19. The vacuum system of claim 18, wherein the canister is coupled to a sensor for detecting a fluid level within the canister.

20. The vacuum system of claim 18, further comprising a vacuum source, wherein the vacuum source, the canister, the vacuum hose, and the vacuum pad are connected in series.

\* \* \* \* \*